(12) United States Patent
Jansen et al.

(10) Patent No.: US 9,757,552 B2
(45) Date of Patent: Sep. 12, 2017

(54) APPLICATOR FOR INSERTING AN IMPLANT

(75) Inventors: Willem Jansen, Lieshout (NL); Maurice Petrus Wilhelmus Tak, Hengelo (NL); Hendricus Johannes Vertegaal, Hengelo (NL); Iris Epkjen Hobo Van Der Graaf, Deventer (NL)

(73) Assignee: MERCK SHARP & DOHME B.V., Haarlem (NL)

( * ) Notice: Subject to any disclaimer, the term of this patent is extended or adjusted under 35 U.S.C. 154(b) by 1650 days.

(21) Appl. No.: 11/795,805

(22) PCT Filed: Jan. 20, 2006

(86) PCT No.: PCT/EP2006/050346
§ 371 (c)(1),
(2), (4) Date: May 27, 2008

(87) PCT Pub. No.: WO2006/077250
PCT Pub. Date: Jul. 27, 2006

(65) Prior Publication Data
US 2010/0298807 A1    Nov. 25, 2010

(30) Foreign Application Priority Data
Jan. 24, 2005   (EP) .................................... 05100418

(51) Int. Cl.
*A61M 37/00* (2006.01)
*A61M 31/00* (2006.01)

(52) U.S. Cl.
CPC ...... *A61M 37/0069* (2013.01); *A61M 31/007* (2013.01)

(58) Field of Classification Search
CPC ...... A61M 37/0069; A61M 2005/3228; A61M 31/007; A61B 17/3468
(Continued)

(56) References Cited

U.S. PATENT DOCUMENTS

| 1,655,158 A | 1/1928 | Muir |
| 4,994,028 A | 2/1991 | Leonard et al. |

(Continued)

FOREIGN PATENT DOCUMENTS

| EP | 0631794 | 1/1995 |
| EP | 1300129 A2 | 4/2003 |

(Continued)

*Primary Examiner* — Emily Schmidt
*Assistant Examiner* — Lauren M Peng
(74) *Attorney, Agent, or Firm* — Hoyng Rokh Monegier LLP; David P. Owen; Ramin Amirsehhi (57) ABSTRACT

The invention pertains to an applicator (1) for inserting an implant, in particular a rod-like implant (2) containing an active substance, under the skin of a human or animal, comprising a housing (3), a cannula (6), a cannula holder (9), an implant (2) accommodated inside the cannula (6) and/or the cannula holder (9), a protective cover (7) for the cannula (6), and a mechanism (22, 23, 7) which, at least after the cover (7) has been removed from the cannula (6), secures the implant (2) inside the cannula (6) and/or cannula holder (9). The mechanism (22, 23, 7) disengages the implant (2) during insertion of the cannula (6) or after the cannula (6) has been inserted. Substantially no lateral force will be exerted during the expelling of the implant from the cannula.

25 Claims, 4 Drawing Sheets

(58) Field of Classification Search
USPC .......................................... 604/11–18, 59–64
See application file for complete search history.

(56) References Cited

U.S. PATENT DOCUMENTS

| | | | |
|---|---|---|---|
| 5,279,554 A | 1/1994 | Turley et al. | |
| 5,279,555 A * | 1/1994 | Lifshey ............. | A61M 37/0069 604/223 |
| 5,395,319 A | 3/1995 | Hirsch et al. | |
| 5,484,403 A | 1/1996 | Yoakum et al. | |
| 5,695,463 A | 12/1997 | Cherif-Cheikh et al. | |
| 5,810,769 A | 9/1998 | Schlegel | |
| 5,827,297 A | 10/1998 | Boudjema | |
| 5,906,599 A | 5/1999 | Kaldany et al. | |
| 6,190,350 B1 * | 2/2001 | Davis ................ | A61M 37/0069 604/61 |
| 6,402,716 B1 | 6/2002 | Ryoo et al. | |
| 6,592,508 B1 | 7/2003 | Ravins et al. | |
| 6,626,863 B1 * | 9/2003 | Berler ........................... | 604/110 |
| 2001/0031940 A1 | 10/2001 | Loos | |
| 2003/0040699 A1 | 2/2003 | Talling et al. | |
| 2003/0059471 A1 * | 3/2003 | Compton et al. ............. | 424/489 |
| 2003/0135153 A1 * | 7/2003 | Hagemeier ....... | A61M 37/0069 604/59 |
| 2003/0233101 A1 * | 12/2003 | Lubock ............ | A61M 37/0069 606/116 |
| 2004/0199140 A1 | 10/2004 | Rue et al. | |

FOREIGN PATENT DOCUMENTS

| | | |
|---|---|---|
| EP | 1666084 A1 | 6/2006 |
| JP | 1997509346 | 9/1997 |
| RU | 4479 U1 | 7/1997 |
| RU | 2192285 C2 | 11/2002 |
| SU | 1183085 A | 10/1985 |
| SU | 1718971 A1 | 3/1992 |
| WO | 2004026106 A | 4/2004 |
| WO | 2004/089458 | 10/2004 |

* cited by examiner

APPLICATOR FOR INSERTING AN IMPLANT

The invention relates to an applicator for inserting an implant, in particular a rod-like implant containing an active substance, under the skin of a human or animal, comprising a housing, a cannula, a cannula holder, an implant accommodated inside the cannula and/or the cannula holder, a protective cover for the cannula, and a mechanism which secures the implant inside the cannula and/or the cannula holder.

Such an applicator is known in the art.

EP 0 631 794 relates to a device for administering implants which comprises an active substance container (denoted by numeral 1) with an injection cannula (6) and a plunger (4). The plunger (4) is arranged in a plunger channel (3). The plunger channel (3) merges continuously into the lumen of the cannula (6). A holding device (5) for the implant (2) is arranged in the end of the plunger channel (3) on the lumen side. The holding device comprises two bolts ("Bolzen 7, 8") that form an obstacle ("Hindernis") for the implant.

US 2001/031940 relates to a device for administering implants. The device is a syringe-like device having a plunger, an injection cannula, and an active substance container therebetween. The active substance container includes two retaining elements for preventing inadvertent dispensing of an implant. The retaining elements are flexible, and may be O-rings.

U.S. Pat. No. 5,484,403 relates to a hypodermic syringe for implanting objects in the bodies of birds, fish, animals, and humans which consists of a barrel, a cannula attached to one end of the barrel, and a plunger that can be moved back and forth within the barrel. A user implants an object by placing the object inside the cannula, making an incision with the cannula, and then pushing on the plunger thereby causing the object to move from the cannula through the incision and into the body. The cannula is provided with a means, in particular crimp regions (denoted by numeral 31), for holding the implant object securely within the cannula from the moment of insertion of the object into the cannula until the moment of implantation.

U.S. Pat. No. 5,395,319 relates to a needle (denoted by numeral 12) with a sharpened point (14) at the tip end a needle holder (16) at the rear end holding the needle, a mandrel (24) which can be displaced inside the needle, and optionally a protective cap (18) enclosing the needle point and detachably attached to the needle holder, with which objects (10) such as long-term preparations, identification tags, or the like are to be inserted in the body of a living being. To ensure that it is unequivocally fixed in position inside the needle, the object is arranged between a closure towards the tip of the needle and, for example, a constriction (20) towards the handling end. At the needle point end, at least a region of the lumen of the needle can be closed off by an ointment-like material containing a medicinally active ingredient, which continues to adhere at least to regions of the object during insertion. This provides at least a preventive measure against inflammation. However, the closure can also be an adhesive material for example, or a silicone stopper.

Many implants, in particular implants that slowly release an active substance over an extended period of time, are delicate. Bolts, O-rings, crimp regions, and other closures inside the lumen of the cannula may cause damage to such delicate implants.

It is an object of the present invention to provide an applicator which, on the one hand, secures the implant inside the cannula and/or the cannula holder and, on the other hand, facilitates avoiding damage to the implant, especially during insertion thereof.

To this end, the applicator according to the present invention is characterised in that the mechanism disengages the implant during insertion of the cannula under the skin of a human or animal or after the cannula has been inserted. It is preferred that the mechanism secures the implant inside the cannula upon removal of the cover and that the mechanism disengages the implant prior to expelling it from the cannula.

Thus, substantially no force will be exerted on the implant as long as the cover is in place, typically throughout storage, and substantially no lateral force will be exerted on the implant as it is expelled from the cannula.

It is further preferred that the mechanism comprises a lever extending along at least part of the cannula, which lever is rotatable and/or slidable and/or flexible between a first position wherein the implant is secured, preferably engaged by the lever itself, inside the cannula and/or the cannula holder and a second position wherein the implant is disengaged.

If the cannula and/or the cannula holder comprises an opening which allows access to the implant and the lever comprises a protrusion in register with this opening, the applicator can be constructed in a relatively straightforward yet effective manner. Furthermore, the protrusion will hinder the cannula from being retracted if no implant is present in the cannula.

In a further preferred embodiment, the lever is biased towards the cannula and/or the cannula holder and (gently) urges the implant against the inner wall of the cannula or the cannula holder.

In a further preferred embodiment, the lever in its first position locks the cannula or the cannula holder, thus preventing movement in the longitudinal direction, and in its second position unlocks the cannula or the cannula holder.

The invention also pertains to an applicator comprising a mechanism which if no implant is present in the cannula and the cannula holder, locks the (removable) cover to the housing. Thus, removal of the cover and hence insertion of a cannula is hindered or even prevented if no implant is present in the cannula.

This applicator preferably comprises a lever extending along at least part of the cannula and rotatable and/or slidable and/or flexible between a position wherein the cover is locked (if no implant is present) and a position wherein the cover is unlocked (if an implant is present).

It is noted that U.S. Pat. No. 5,906,599 discloses a device for delivering biological agents which includes a cannula for insertion into tissue having a distal end with a notch formed therein. A flexible membrane extending across the cannula notch has a surface for supporting a quantity of a biological agent. A displacement member is disposed within the cannula for displacing the support surface of the membrane laterally with respect to the cannula to deliver the biological agent with precision to a tissue site or body cavity.

U.S. Pat. No. 1,655,158 discloses an instrument for implanting radon seeds which is composed of three elements, namely, an implanter (1), a trocar (2), and a plunger (3). The implanter comprises a tubular body portion (4) and a needle (5).

WO 2004/089458 discloses a device for inserting implantable objects beneath the skin of a patient which includes a handle for grasping the device and a base connected to the handle. The base comprises a post, a cannula, and a flexible actuator positioned in an angled track.

WO 01/68168 discloses a disposable device for inserting one or several implants, said device comprising a tubular cannula (10) provided with a tip (11), said cannula also serving as a container for the implants, a plunger (20), and a handle (30) having a first end (31) directed towards the cannula (10) and a second end (32) directed away from the cannula.

U.S. Pat. No. 5,827,297 discloses a device for transplanting small diameter hair grafts using a hand-held cutting instrument having a body holding the tool, a rotary cylindrical tool, and a drive assembly capable of driving the tool in rotation with respect to the body.

U.S. Pat. No. 6,402,716 discloses a syringe assembly which includes a protection member to contain the ejecting elongated rod, a cover member to cover the needle with a small rod formed inside the closed end thereof, the small rod extending at a predetermined distance towards the needle part to keep the same in place and to contain the injection materials therein.

U.S. Pat. No. 5,695,463 discloses an injection device for intramuscular or subcutaneous injection of solid or semi-solid medicaments. The device includes a main body member having a needle attached thereto. A protective sleeve covers the needle and retracts into the main body member when the device is pressed against the skin of a patient.

U.S. Pat. No. 5,279,554 discloses a device for implanting an object, such as a hormone pellet or an electronic transponder, beneath the skin of an animal, which device includes a hollow needle (1) with an actuating rod (11) slidable therein, a cover (2) movable relative to the needle to enable at least the sharp end of the needle to be shrouded, and a locking mechanism in the form of an abutment (10) movable into a rebate (6), from which it cannot then return.

U.S. Pat. No. 6,592,508 discloses an implantation device which includes an implantation needle having a bore extending longitudinally therethrough from a proximal end to a distal end, the needle bore being adapted to permit at least one seed to pass therethrough.

The invention will now be explained in more detail with reference to the drawings, which schematically show two preferred embodiments according to the present invention.

FIGS. 1 to 8 show a preferred disposable applicator 1 for inserting an implant 2, in particular a rod-like implant containing an active substance, such as a contraceptive, under the skin of a human. The applicator 1 comprises a housing 3 consisting of two half-shells 4, 5, a metal cannula 6 (FIG. 2) accommodating the implant 2, a protective cover 7 (FIGS. 1 and 4) comprising a pin 7A extending into the tip of the cannula 6 to restrict the freedom of movement of the implant 2, and an actuator 8 for retracting the cannula 6 into the housing 3. The cannula 6 is fixed to a cannula holder 9, which is slidably received inside the housing 3. To this end, the inner wall of each of the half-shells 4, 5 is provided with two parallel and longitudinal guides 10 (FIG. 6) and the cannula holder 9 is provided with corresponding longitudinal grooves 11. The cannula holder 9 is connected to the actuator 8 by means of a flexible element 12, which, in this example, forms an integral whole with the cannula holder 9 and the actuator B. Depending on the configuration of the applicator, it may be more advantageous to employ a rigid element and/or a separate actuator, flexible element, and needle holder which are connected upon assembly of the applicator.

Figure 1:
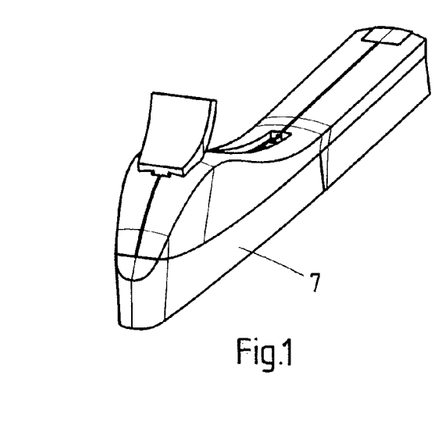
FIG. 1 is a perspective view of a first embodiment of an applicator in accordance with the present invention.
Figure 2:
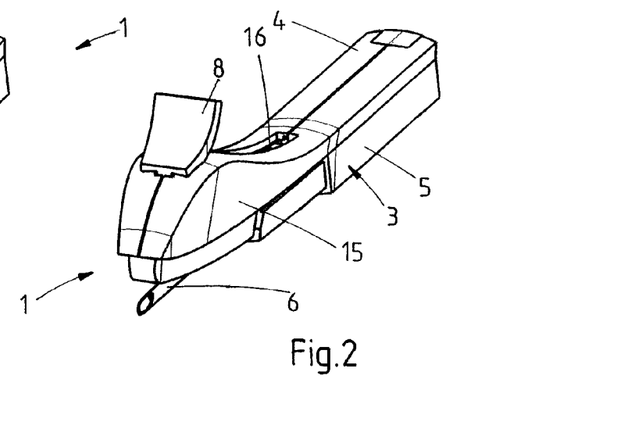
FIG. 2 is a perspective view of the same applicator as in FIG. 1, with its protective cover removed.
Figure 3:
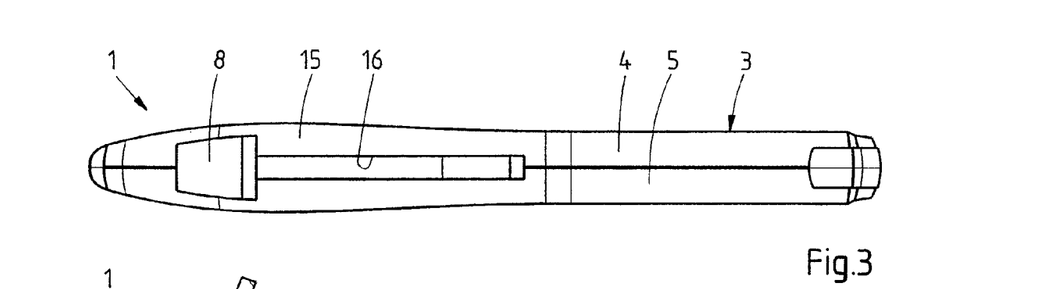
FIGS. 3 and 4 are, respectively, a top view and a cross-sectional side view of the preferred applicator of FIG. 1, with the cannula in art extended position.
Figure 4:
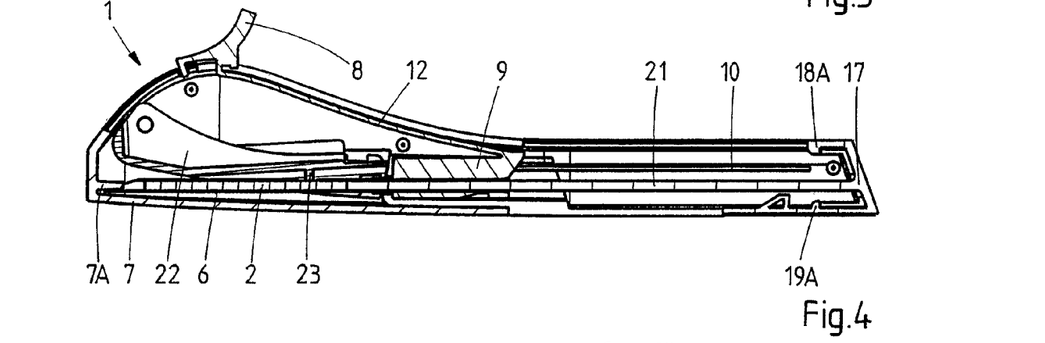
Figure 5:
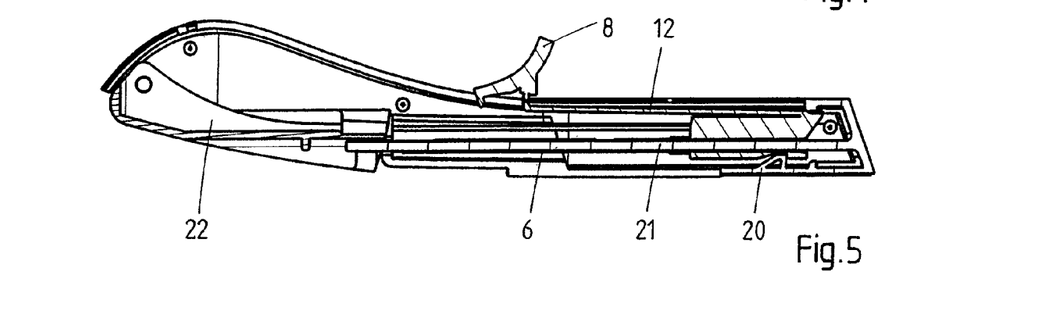
FIG. 5 is a cross-sectional side view of the preferred applicator of FIG. 1, with the cannula in a retracted position.
Figure 6:
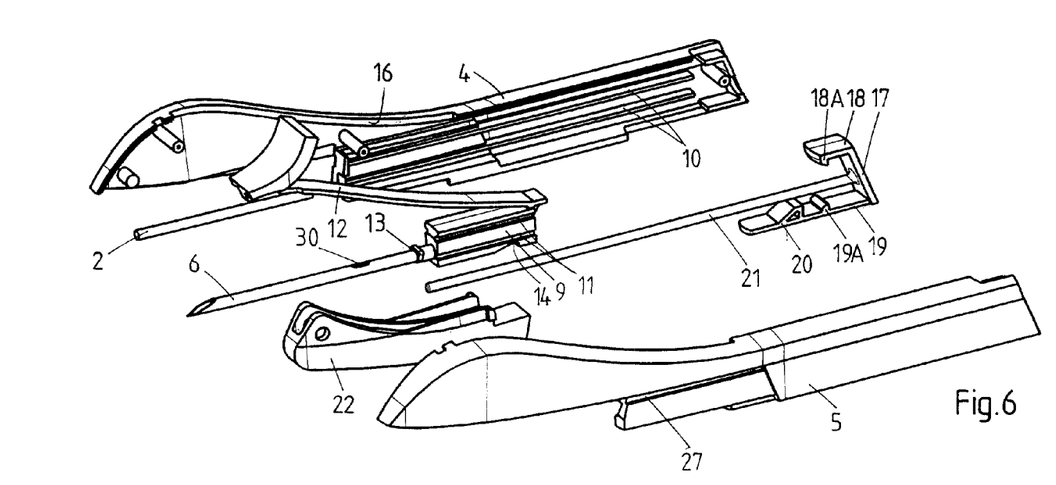
FIG. 6 is an exploded view of the preferred applicator of FIG. 1.
Figure 7:
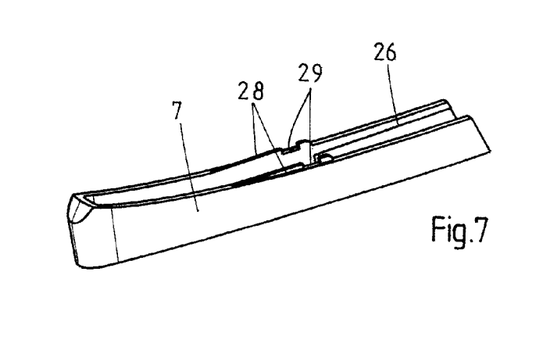
FIG. 7 is a perspective view of the protective cover.
Figure 8:
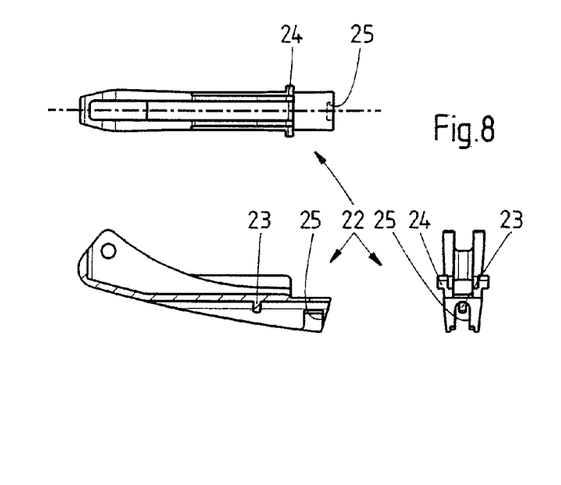
FIG. 8 provides top, cross-sectional, and rear views of a lever used in the preferred applicator of FIG. 1.

As can be seen in FIG. 6, the cannula holder 9 comprises a collar 13 on its front (distal) end, at the transition to the cannula 6, and a notch 14 on its bottom surface near its rear (proximal) end. As will be explained below, these features serve to lock the cannula holder, and hence the cannula, in an extended and a retracted position, respectively.

The housing 3 comprises a handle 15 for grasping and manoeuvring the cannula 6 during insertion. The handle 15 extends above, i.e. along and spaced from the cannula 6, preferably to near the distal end of the cannula 6, and facilitates insertion of the cannula 6 and/or accurate positioning of the implant 2. To further enhance grasping the applicator and manoeuvring the cannula, it is generally preferred that the thickness of the handle and/or the bending stiffness are greater than the thickness and the bending stiffness of the cannula, respectively.

On top of the handle 15, a track 16 is provided for guiding the actuator 8. Guides (not shown) may be included, preferably just below the track 18, to retain and guide the flexible element 12.

A bracket 17 has been inserted in and snap-fitted to the rear end of the housing 3, by means of two resilient fingers 18, 19, each provided with a protrusion 18A, 19A. The lower finger 19 further comprises, near its end, a wedge-shaped protrusion 20. The bracket 17 also comprises a rod 21, which extends through the greater part of the housing 3 and into the cannula holder 9 and the cannula 6. In this example, the length of the rod 21 is adjusted to the length of the lumen of the cannula holder 9 and the cannula 6 and the length of the implant 2, such that when the cannula 6 is in the extended position, the implant 2 is fully contained inside the cannula 6 and typically abuts the distal end of the rod 21. When the cannula 6 is in the retracted position, the implant 2 is completely expelled from the cannula 6 and the distal end of the rod 19 extends from the distal end of the (retracted) cannula 6.

A lever 22 has been pivotally connected to the front end of the handle 15. The lever 22 is gently biased towards the cannula 6 by means of a metal spring (not shown) extending between the lever 22 and an inner wall of the handle 15. In the present preferred example, the lever 22 interacts with the protective cover 7, the implant 2, and the cannula holder 9. To this end, the lever 22 comprises (from left to right in FIG. 8), a first protrusion 23 on its lower wall, a pair of lateral protrusions 24 on its upper rim, and a vertically extending slot 25 in its rear wall.

The protective cover 7 (FIG. 7) on its inner walls comprises a pair of ridges 26 which, in combination with corresponding slots 27 on the outside of the half-shells 4, 5, impose sliding engagement between the cover 7 and the housing 3. The cover 7 further comprises, on its upper rim, a pair of keys 28, each interrupted by a notch 29.

Finally, the cannula 6 comprises an opening 30 (FIG. 6) which allows the protrusion 23 to engage the implant 2 and thus to gently urge the implant 2 against the inner wall of the cannula 6.

With the protective cover 7 in place, the lateral protrusions 24 of the lever 22 are supported by the keys 28 and the first protrusion 23 is just clear of the implant 2.

If the protective cover 7 is removed, i.e. slid in longitudinal direction and away from the housing 3, the keys 28 will slide under the lateral protrusions 24. If no implant 2 is present inside the cannula 6, the protrusion 23 on the lever 22 is free to enter the cannula 6 through the opening 30. I.e., the lever 22 will drop when the lateral protrusions 24 reach the notches 29, thus blocking further movement of the cover 7, preventing the same from being removed and preventing the applicator from being used any further. If an implant 2 is present, the lever 22 will be lowered only very slightly, with the lateral protrusions 24 still clear of the notches 29, and yet causing the first protrusion 23 to rest, through the opening 30, on the implant 2, thus, on the one hand, allowing the cover 7 to be removed and, on the other, gently urging the implant 2 towards the inner wall of the cannula 6, i.e. securing the implant 2 inside the cannula 6.

A medical professional can now take the applicator 1 in one hand, e.g. with the thumb on one side of the handle 15 and the fingers on the other side, and insert the cannula 6 under the skin of a patient. During insertion, the handle 15 enables coordinated manoeuvring of the applicator 1 and the cannula 6 and careful lifting of the skin to facilitate insertion of the implant 2 at an appropriate depth. Skin on top of the cannula 6 will lift the lever 22 to such an extent that contact between the protrusion 23 and the implant 2 is removed, i.e. the implant 2 is disengaged without requiring a specific action by the medical professional, and the slot 25 in the rear wall of the lever 22 clears the collar 13 on the front portion of the cannula holder 9, thus unlocking the latter. Subsequently, the actuator 8 is unlocked and the cannula 6 is pulled rearwards, e.g. with the index finger of the hand that holds the applicator 1. During this rearward motion, the implant 2 abuts the distal end of the rod 21 and maintains its longitudinal position. Only limited friction occurs between the implant 2 and the inner wall of the cannula 6 and substantially no lateral forces are exerted on the implant 2. When the needle holder 9 arrives at the fully retracted position, the finger 19 (part of bracket 17) will flex downwards and the protrusion 20 on that finger 19 will snap into the notch 14 on the lower surface of the needle holder 9, preferably sounding an audible click and indicating to the medical professional that the implant 2 has been inserted and that the applicator 1 can be removed and discarded. The said protrusion 20 and notch 14 also form a lock that prevents the applicator 1 from being used again.

Figure 9:
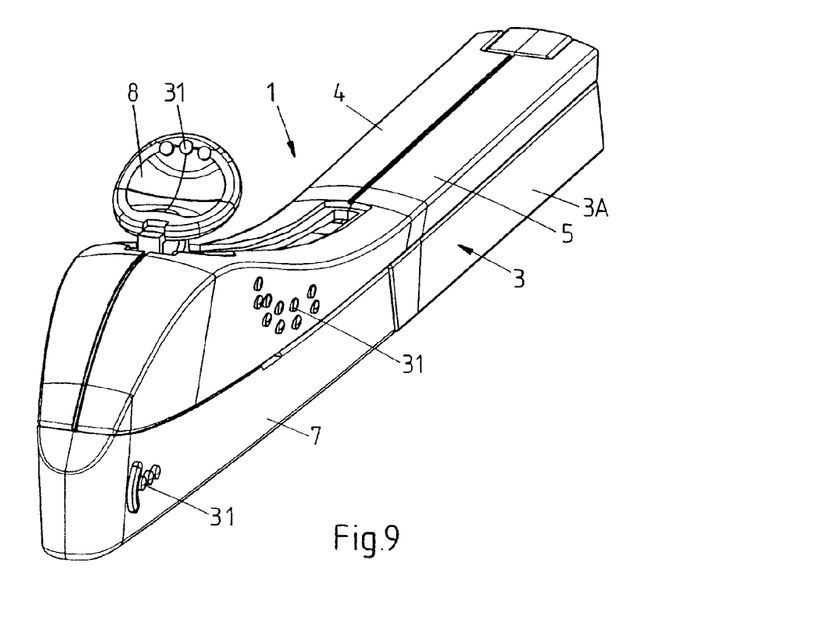
FIG. 9 is a perspective view of a second embodiment of an applicator in accordance with the present invention.
Figure 10:
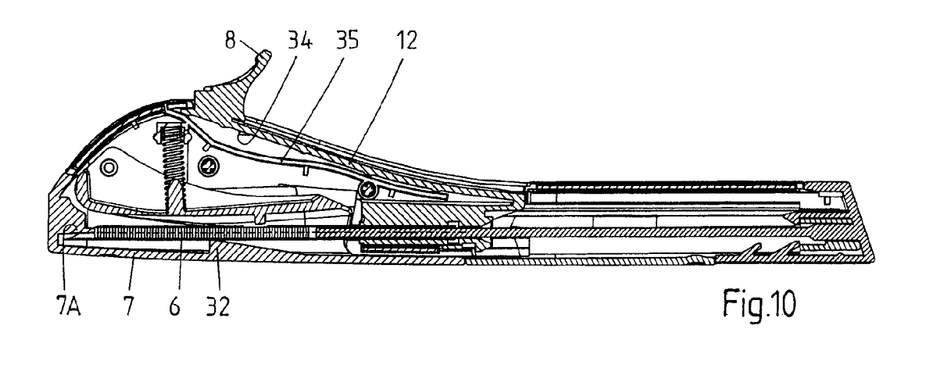
FIG. 10 is a cross-sectional side view of the preferred applicator of FIG. 9, with the cannula in an extended position.
Figure 11:
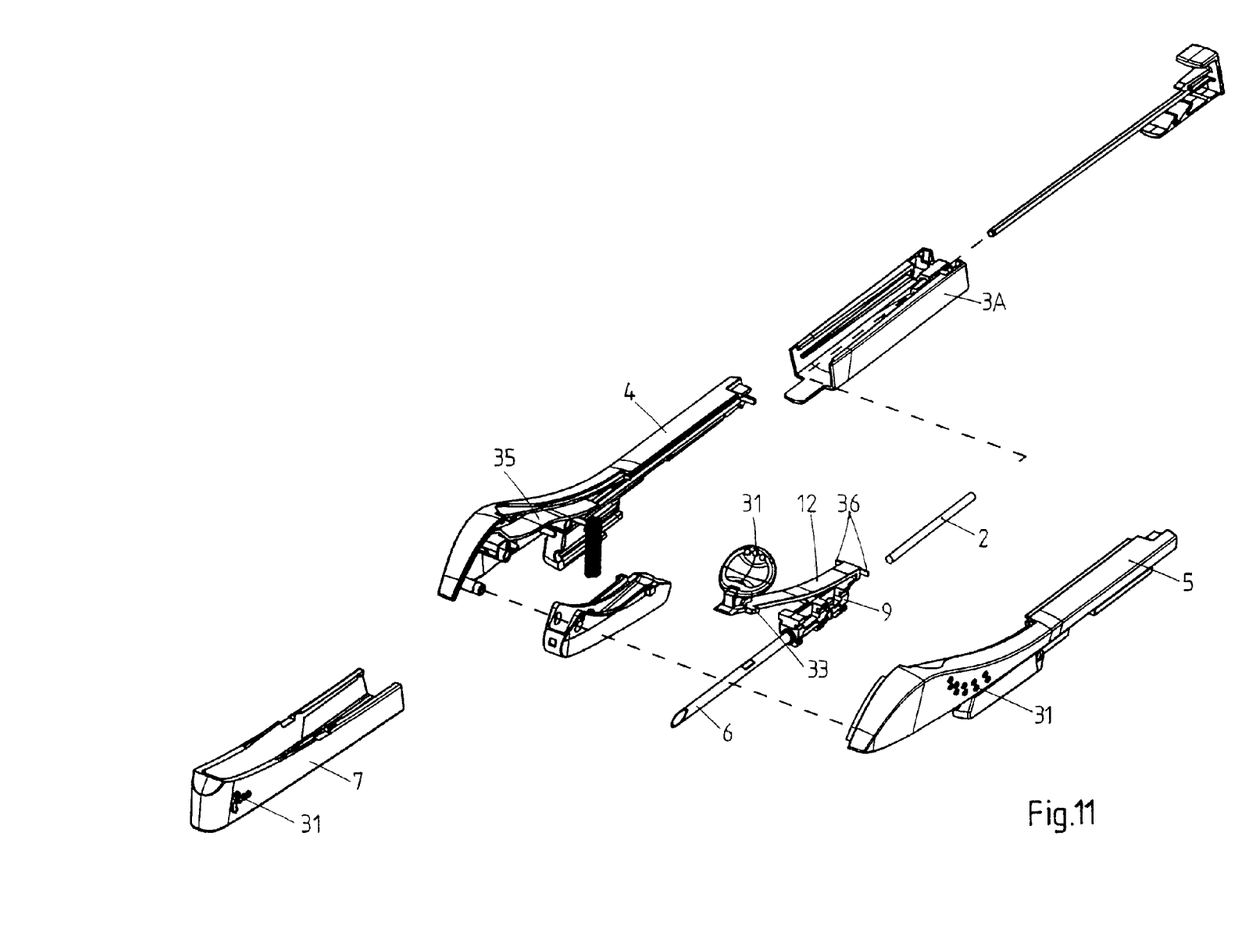
FIG. 11 is an exploded view of the preferred applicator of FIG. 9.

FIGS. 9 to 11 show a second embodiment of an applicator in accordance with the present invention. The main differences from the first embodiment will be discussed below. Elements that are at least substantially identical to those in the first embodiment are denoted by the same numeral.

In the second embodiment, the housing 3 consists of two side shells 4, 5 welded together (ultrasonically) and a separate rear section 3A, which has been snap fitted to the side shells 4, 5. The handle 15 and the protective cover 7 have been provided, on either side, with a relief, in this example a pattern of protrusions 31, to enhance grip and to provide guidance as to where to grasp these respective parts 15, 7. Similar protrusions 31 have been provided on the (upper) rim of the actuator 8.

Further, the cover 7 comprises, on its inner bottom wall, a stay 32 preferably having, in its top surface, a V-shaped groove extending in the longitudinal direction of the applicator 1. Upon placing the protective cap 7 onto the housing 4, 5, the stay 32 slightly lifts the cannula 6 and reproducibly defines the lateral position and height of the tip of the cannula 6 with respect to the pin 7A, thus preventing contact between the tip of the needle and the inner walls of the cover 7.

The flexible element 12, interconnecting the actuator 8 and the cannula holder 9, comprises, preferably just below the actuator 8 and on either side of the flexible element 12, lateral protrusions 33. The inner wall of the housing 4, 5 in turn comprises two corresponding stops 34, which prevent the protrusions 33 from passing and hence the actuator 8 from being pulled rearwards unintentionally. The lateral protrusions 33 and stops 34 also prevent the cannula holder 9 and the cannula 6 from being pushed rearwards during insertion.

A guide 35 for retaining and guiding the flexible element 12 is provided just below the track 16. The guide 35 is shaped to provide sufficient room below the actuator 8 to enable it to flex sufficiently far downwards and allow the lateral protrusions 33 to pass the stops 34, upon pushing the actuator 8 down. Retracting the cannula 6 may thus be performed in one flowing movement, i.e. upon applying pressure to the actuator 8, typically with an index finger, the actuator 8 flexes downwards, clearing the stops 34, and subsequently rearwards to the retracted position.

In contrast to the first embodiment, no collar (13) is present on the front (distal) end of the cannula holder 9. Instead, two resilient lips 36 are provided on the rear (proximal) end of the cannula holder 9. The inner sidewalls of the housing 4, 5 in turn comprise two corresponding stops (not shown) that block rearward motion of the lips 33 and hence define the longitudinal position of the cannula holder 9 in rearward direction. It is preferred that this mechanism urges the cannula holder 9 into its most forward position, so as to prevent the implant 2 from extending from the cannula 6. Upon actuation, the lips 33 will flex inwards and past the stops.

As will be clear from the explanations above, the preferred applicators according to the present invention (automatically) secure the implant inside the cannula upon removal of the protective cover and (again, automatically) disengage the implant when insertion of the cannula under the skin of a patient has been substantially completed.

Thus, the applicator according to the present invention is especially suitable for use with delicate implants, in particular implants that slowly release an active substance over an extended period of time. A preferred example of such an implant is a single-rod contraceptive implant that provides protection against pregnancy for an extended period of time, e.g. 3 years. It consists of a non-biodegradable rod measuring 40 mm in length and 2 mm in diameter. After insertion, the rod slowly releases a progestogenic hormone, viz. etonogestrel.

The invention is not restricted to the above-described embodiments, which can be varied in a number of ways within the scope of the claims. For instance, instead of pivotally mounting the lever to the housing, the lever can be made, either wholly or partially, from a flexible material that allows it to flex between its various positions.

The invention claimed is:

1. An applicator for inserting a rod-like implant containing an active substance, under the skin of a human or animal, comprising
   a housing,
   a cannula,
   a cannula holder,
   an implant accommodated inside the cannula or the cannula holder,
   a protective cover for the cannula, and
   a mechanism,
   wherein the cannula comprises a tube having a hollow interior along an axial length of the tube and terminating in an opening at an axial end of the tube,
   wherein the implant is slidable through the hollow tube along the axial length to exit through the opening for insertion of the implant,
   wherein removal of the cover causes the mechanism to engage with the implant to secure the implant inside the cannula or the cannula holder to prevent exit of the implant through the opening, wherein the mechanism disengages the implant during insertion of the cannula or after the cannula has been inserted and prior to movement of the implant with respect to the cannula for expelling the implant from the cannula.

2. The applicator according to claim 1, wherein the mechanism exerts substantially no force on the implant prior to removal of the cover and secures the implant inside the cannula upon removal of the cover.

3. The applicator according to claim 1, wherein the mechanism comprises a lever extending along at least part of the cannula, which lever is rotatable or slidable or flexible between a first position wherein the lever engages with the implant so that the implant is secured inside the cannula or the cannula holder and a second position wherein the lever is disengaged from the implant.

4. The applicator according to claim 3, wherein the cannula or the cannula holder comprises an opening which allows access to the implant, and the lever comprises a protrusion in register with this opening to protrude through the opening to engage with the implant.

5. The applicator according to claim 4, wherein the lever is biased towards the cannula or the cannula holder and urges the implant against the inner wall of the cannula or the cannula holder.

6. The applicator according to claim 3, wherein the cover, when installed, forces the lever into its second position.

7. The applicator according to claim 3, wherein the lever in its first position locks the cannula or cannula holder, and in its second position unlocks the cannula or cannula holder.

8. The applicator according to claim 7, wherein the lever comprises at least one protrusion or notch, the cannula or the cannula holder comprises respectively at least one notch or protrusion, and wherein at least one respective notch and protrusion interlock in the first position of the lever.

9. The applicator according to claim 1, comprising a rod mounted on or in the housing and at least partially inside the cannula, and an actuator for sliding the cannula and the rod relative to each other.

10. The applicator according to claim 1 received inside a sterile package.

11. The applicator according to claim 1, wherein the implant is a non-biodegradable rod measuring 40 mm in length and 2 mm in diameter and containing etonogestrel.

12. The applicator according to claim 1, further comprising a second mechanism which, if no implant is present in the cannula or the cannula holder, locks the cover to the housing.

13. The applicator according to claim 1, further comprising an actuator for retracting the cannula into the housing for expelling the implant from the opening of the cannula.

14. The applicator according to claim 1, wherein the implant contains etonogestrel.

15. An applicator for inserting a rod-like implant containing an active substance, under the skin of a human or animal, comprising
   a housing,
   a cannula,
   a cannula holder,
   an implant accommodated inside the cannula or the cannula holder,
   a protective cover for the cannula, and
   a mechanism,
   wherein the cannula comprises a tube having a hollow interior along an axial length of the tube and terminating in an opening at an axial end of the tube,
   wherein the implant is slidable through the hollow tube along the axial length to exit through the opening for insertion of the implant,
   wherein the mechanism, after the cover has been removed from the cannula, engages with the implant to secure the implant inside the cannula or the cannula holder to prevent exit of the implant through the opening, wherein the mechanism disengages the implant during insertion of the cannula or after the cannula has been inserted and prior to movement of the implant with respect to the cannula for expelling the implant from the cannula, and
   wherein the mechanism comprises a lever extending along at least part of the cannula, which lever is rotatable or slidable or flexible between a first position wherein the lever engages with the implant so that the implant is secured inside the cannula or the cannula holder and a second position wherein the lever is disengaged from the implant, and
   wherein the housing comprises a handle extending above at least part of the cannula and wherein, the lever is rotatably connected to the distal end of the handle.

16. A method for inserting an implant under the skin of a human or animal using an applicator:
   uncovering the cannula;
   securing the implant inside a cannula or cannula holder using a mechanism which engages the implant, after uncovering the cannula;
   inserting the cannula beneath the skin;
   disengaging the mechanism from the implant during insertion of the cannula or after the cannula has been inserted without moving the implant with respect to the cannula; and
   subsequently sliding the disengaged implant along an axial length of a hollow interior of the cannula to expel the implant from an opening at an axial end of the cannula;
   wherein securing the implant inside the cannula or cannula holder comprises preventing exit of the implant through the opening;
   the method further comprising removing a cover from the cannula prior to inserting the cannula beneath the skin, whereby removal of the cover causes the mechanism to engage with the implant to secure the implant.

17. The method of claim 16, further comprising replacing the cover onto the cannula after expelling the implant, whereby replacing of the cover without an implant being present in the cannula causes locking of the cover over the cannula.

18. The method of claim 16, further comprising accommodating the implant inside the cannula or the cannula holder while exerting substantially no force on the implant prior to removal of the cover.

19. The method according to claim 16, further comprising using an actuator to retract the cannula into the housing for expelling the implant from the opening of the cannula.

20. The method according to claim 16, wherein the implant is a non-biodegradable rod measuring 40 mm in length and 2 mm in diameter and containing etonogestrel.

21. The applicator for inserting a rod-like implant containing an active substance, under the skin of a human or animal, comprising
    a housing,
    a cannula,
    a cannula holder,
    an implant accommodated inside the cannula or the cannula holder,
    a protective cover for the cannula, and
    a mechanism,
    wherein the cannula comprises a tube having a hollow interior along an axial length of the tube and terminating in an opening at an axial end of the tube,
    wherein the implant is slidable through the hollow tube along the axial length to exit through the opening for insertion of the implant,
    wherein the mechanism, after the cover has been removed from the cannula, engages with the implant to secure the implant inside the cannula or the cannula holder to prevent exit of the implant through the opening, wherein the mechanism disengages the implant during insertion of the cannula or after the cannula has been inserted and prior to movement of the implant with respect to the cannula for expelling the implant from the cannula, and
    wherein the mechanism comprises a lever extending along at least part of the cannula, which lever is rotatable or slidable or flexible between a first position wherein the lever engages with the implant so that the implant is secured inside the cannula or the cannula holder and a second position wherein the lever is disengaged from the implant, and wherein the lever is positioned so that the lever contacts the skin of the human or animal during insertion of the cannula to rotate the lever to the second position.

22. A method of contraception comprising inserting an implant containing etonogestrel under the skin of a human or animal using an applicator comprising:
    a housing, a cannula, a cannula holder, an implant, wherein the implant is accommodated inside the cannula or the cannula holder, a protective cover for the cannula, and a mechanism, wherein the cannula comprises a tube having a hollow interior along an axial length of the tube and terminating in an opening at an axial end of the tube, wherein the implant is slidable through the hollow tube along the axial length to exit through the opening for insertion of the implant, wherein removal of the cover causes the mechanism to engage with the implant to secure the implant inside the cannula or the cannula holder to prevent exit of the implant through the opening, wherein the mechanism disengages the implant during insertion of the cannula or after the cannula has been inserted and prior to movement of the implant with respect to the cannula for expelling the implant from the cannula.

23. The applicator according to claim 22, wherein the implant is a non-biodegradable rod measuring 40 mm in length and 2 mm in diameter.

24. The method of claim 22 wherein the mechanism comprises a lever extending along at least part of the cannula, which lever is rotatable or slidable or flexible between a first position wherein the lever engages with the implant so that the implant is secured inside the cannula or the cannula holder and a second position wherein the lever is disengaged from the implant, and wherein the housing comprises a handle extending above at least part of the cannula and wherein, the lever is rotatably connected to the distal end of the handle.

25. The method of claim 22 wherein the mechanism comprises a lever extending along at least part of the cannula, which lever is rotatable or slidable or flexible between a first position wherein the lever engages with the implant so that the implant is secured inside the cannula or the cannula holder and a second position wherein the lever is disengaged from the implant, and wherein the lever is positioned so that the lever contacts the skin of the human or animal during insertion of the cannula to rotate the lever to the second position.

* * * * *